US00PP09148P

United States Patent [19]

Kientzler

[11] Patent Number: Plant 9,148

[45] Date of Patent: May 30, 1995

[54] IMPATIENS PLANT NAMED TANNA

[75] Inventor: Ludwig Kientzler, Gensingen, Germany

[73] Assignee: Paul Ecke Ranch, Inc., Encinitas, Calif.

[21] Appl. No.: 280,260

[22] Filed: Jul. 25, 1994

[51] Int. Cl.[6] ..... A01H 5/00
[52] U.S. Cl. ..... Plt./87.6
[58] Field of Search ..... Plt. 87.6

[56] References Cited

U.S. PATENT DOCUMENTS

| | | | |
|---|---|---|---|
| P.P. 6,728 | 4/1989 | Kientzler | Plt./87.6 |
| P.P. 8,283 | 6/1993 | Kientzler | Plt./87.6 |
| P.P. 8,398 | 9/1993 | Guillen | Plt./87.6 |
| P.P. 8,467 | 11/1993 | Kientzler | Plt./87.6 |

*Primary Examiner*—James R. Feyrer
*Attorney, Agent, or Firm*—Foley & Lardner

[57] ABSTRACT

A new and distinct cultivar of New Guinea impatiens named Tanna, particularly characterized by its compact growth habit with excellent branching characteristics, large, orange-red flowers, early flowering and very floriferous habits, dark green foliage, and suitability to 4 inch and 6 inch pots, and 8 inch hanging basket cultures.

1 Drawing Sheet

The present invention relates to a new and distinct cultivar of plant known as impatiens and commercially known as New Guinea impatiens. The new cultivar is known by the cultivar name Tanna, and was developed by the inventor Ludwig Kientzler in Gensingen, Federal Republic of Germany by crossing the cultivar designated JF 333 (seed parent) with the cultivar RI 279 (pollen parent).

Asexual reproduction by terminal (stem tip) cuttings taken by me or under my supervision at Gensingen, Federal Republic of Germany, has shown that the unique features of this new impatiens are stabilized and are reproduced true to type in successive propagations.

The following characteristics distinguish the new impatiens from both its parent varieties and other cultivars of this general type known and used in the floriculture industry:

1. Compact growth habit with excellent branching characteristics. Plants in 16.5 cm pots were 20 cm tall and 38 cm wide, eight weeks after first flowering.
2. Large, orange-red flowers. Open flowers measure up to 5.5 cm in diameter.
3. Early flowering and very floriferous. Plants in 16.5 cm pots were in flower 6 weeks after planting.
4. Dark green foliage.
5. Well suited both to 4" and 6" pot, and 8" hanging basket cultures.

Tanna is similar in many respects to Barbados, disclosed in U.S. Plant Pat. No. 8,467. The flower color of Tanna is an orange-red, similar in color to Barbados. The leaf color of Tanna is much darker than Barbados. Tanna has a more compact growth habit, darker leaves and blooms earlier than Barbados. Reference is made to chart A at the end of the specification which compares certain characteristics of Tanna with the same characteristics of Barbados.

The accompanying colored photograph is a top perspective view of the new cultivar, showing color as true as it is reasonably possible to obtain in a colored reproduction of this type.

The following is a detailed description of my new impatiens cultivar based on plants grown under commercial practice in Encinitas, Calif. Plants were started as rooted cuttings and were transplanted in mid-November into 16.5 cm (6.5 inch) pots, one pot per plant. By mid-January, plants were growing vigorously and were in flower. The values, measurements and observations noted below were taken from plants in full bloom in mid-February.

Color references are made to the Royal Horticultural Society Colour Chart (RHS), except where general terms of ordinary dictionary significance are used.

Parentage: Cross between JF 333 (seed) and RI 279 (pollen).

Asexual reproduction:

A. *Cutting type.*—Tip, with stems 2–3 cm long and developing to 4–5 cm after 21 days in propagation.

B. *Time to initiate roots.*—8–10 days at 23° C.; nicely developed root mass in 18–21 days.

C. *Rooting habit.*—Numerous, fibrous, adventitious roots from the stem.

Plant description:

A. *Form.*—Symmetrical, bush shaped, flowering herb, with self-branching characteristics giving the plant a full appearance. Pinching is not recommended since it does not enhance branching and only delays flowering by removing flower buds.

B. *Habit of growth.*—Vigorous, self-branching habit, producing whorls of leaves and flowers. Growth is indeterminate and flowering is continuous.

C. *Foliage description.*—Leaves are simple. Lower leaves on stems in whorls of 4. Higher on stem, leaves in whorls of predominately 8. 1. Leaf shape: Broadly elliptic to ovate. Leaf blade tips are acuminate; bases of immature leaves are acute, mature leaves, attenuate. 2. Leaf blade size: Mature leaves 11–12 cm long and 4.5 cm wide. 3. Petiole length: 2–2.5 cm. 4. Leaf Margin: Ciliated and finely serrated. 5. Leaf texture: Slightly rugose. a. Upper surface: Glabrous. b.

Under surface: Glabrous. 6. Leaf color: Dark green with a red petiole. a. Upper surface: Darker than 147A. b. Under surface: Greyed purple, near 183A. 7. Venation: Pinnate.

Flowering description:

A. *Flowering habits.*—Very floriferous. Flowering is continuous. Flowers develop progressively around the whorl of leaves, taking 5–7 days from buds which show color, to bloom. Flowers are single and large, lasting for 2–3 weeks.

B. *Natural flowering season.*—Flowering is indeterminate and occurs throughout the year. Quantity of flowers increases with increasing light intensity and duration. However, floriferousness may wane during hot summer days in temperate climates.

C. *Flower buds.*—Ellipsoidal and covered with 3 sepals plus rudimentary sepals fused into the under surface of the superior petal. A spur originates from the base of the inferior sepal. Spur is red and 5 cm long.

D. *Flowers borne.*—Singly, on dark red pedicels 4–4.5 cm long.

E. *Quantity of flowers.*—One flower per leaf. Flowers occur progressively around the whorl of leaves so that tight buds to mature flowers are visible at the same time.

F. *Petals.*—Petals open nearly perpendicular to the pedicel so that the plane of the flower surface is nearly flat. 1. Number of petals: Five (5) petals, all overlapping. 2. Shape: All petals are heart-shaped. Superior petal has a broad base. Other petals have a pointed base. 3. Color: Bright orange with a pinkish eye. a. Upper surface: Orange, between 33A and 33B. Base of petals purplish red, near 64A. Pink eye near 65A. b. Under surface: Near 35A. 4. Flower size: Up to 5.5 cm in diameter.

G. *Reproductive organs.*—Flowers are monoecious. 1. Stamens: Five (5), broad and fused to form a tube around the ovary; red in color. 2. Anther: Hooded and cream colored. 3. Pollen: Cream colored. 4. Stigma: Five pointed star, colorless. 5. Styles: Very short. 6. Ovary: 5-celled, 4–5 mm long until fertilized. Grows to 1 cm or longer after fertilization; green.

Resistance to disease: Good resistance to common stem and root diseases, Rhizoctonia and Pythium. Botrytis may be a problem in humid or mist propagation environments, but no greater than with other New Guinea impatiens cultivars.

CHART A

| | Tanna | Barbados |
|---|---|---|
| Flower Color | RHS 33 A-B | RHS 33 A-B |
| Plant Height (above the pot) | 20 cm | 25 cm |
| Plant Width | 38 cm | 43 cm |
| Weeks to flower | 6 wks | 7 wks |
| Flower Diameter | 5.5 cm | 5.5 cm |

I claim:

1. A new and distinct cultivar of New Guinea impatiens named Tanna, as illustrated and described.

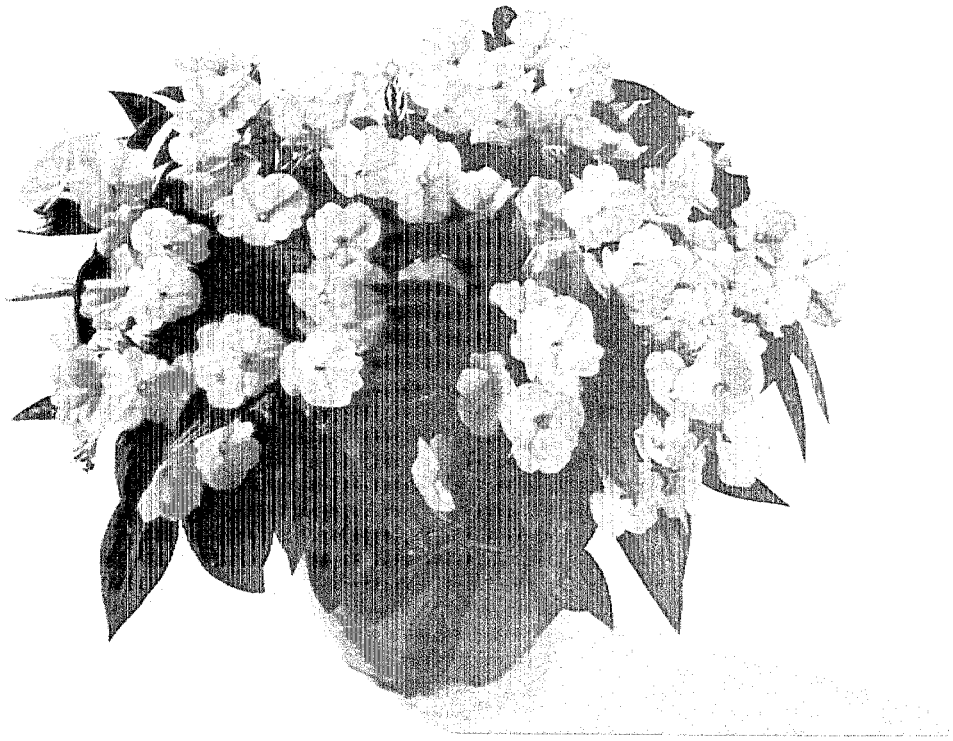

* * * * *